United States Patent
Powlan

(10) Patent No.: US 8,470,005 B1
(45) Date of Patent: Jun. 25, 2013

(54) HIP NAIL SUPPORT ASSEMBLY

(71) Applicant: Roy Y. Powlan, Lafayette, CA (US)

(72) Inventor: Roy Y. Powlan, Lafayette, CA (US)

(*) Notice: Subject to any disclaimer, the term of this patent is extended or adjusted under 35 U.S.C. 154(b) by 0 days.

(21) Appl. No.: 13/694,109

(22) Filed: Oct. 31, 2012

(51) Int. Cl.
  *A61B 17/74* (2006.01)
  *A61B 17/76* (2006.01)
  *A61B 17/78* (2006.01)
  *A61B 17/80* (2006.01)
  *A61B 17/84* (2006.01)

(52) U.S. Cl.
  USPC ......... 606/286; 606/63; 606/65; 606/66; 606/67; 606/68; 606/289; 606/292; 606/293

(58) Field of Classification Search
  USPC ......... 606/63, 65, 66, 67, 68, 70, 71, 281, 606/282, 286, 289–293, 302, 306, 313, 314, 606/320; 411/57.1, 55, 354; 403/367–371
  See application file for complete search history.

(56) References Cited

U.S. PATENT DOCUMENTS

| | | | |
|---|---|---|---|
| 4,432,358 A | 2/1984 | Fixel | |
| 5,007,910 A | 4/1991 | Anapliotis | |
| 5,041,116 A | 8/1991 | Wilson | |
| 5,324,292 A | 6/1994 | Meyers | |
| 5,957,642 A * | 9/1999 | Pratt | 411/55 |
| 6,645,209 B2 | 11/2003 | Hall, IV | |
| 7,503,919 B2 | 3/2009 | Shaw | |
| 7,670,341 B2 | 3/2010 | Leyden | |
| 8,182,484 B2 | 5/2012 | Grant | |
| 2008/0255559 A1 * | 10/2008 | Leyden et al. | 606/62 |

* cited by examiner

*Primary Examiner* — Kevin T Truong
*Assistant Examiner* — Tracy Kamikawa

(57) ABSTRACT

The assembly supports the trailing end of a lag screw or hip nail device being used to immobilize a hip fracture, and enables the compression of the fractured bone ends together, thereafter enabling sliding of the femoral head together with the lag screw or hip nail laterally, while simultaneously limiting their rotation, thereby promoting healing of the fracture.

4 Claims, 2 Drawing Sheets

HIP NAIL SUPPORT ASSEMBLY

FIELD OF THE INVENTION

This invention relates to an apparatus for use in the treatment of fractures of the proximal femur, specifically, an apparatus for supporting the trailing end of hip screws or nails that have been inserted across a fracture in the neck or peritrochanteric region of the proximal femur.

BACKGROUND OF THE INVENTION

Fractures of the proximal femur, especially those of the neck region are notoriously difficult to treat successfully partly because of poor circulation of blood to the head and neck. Lag screws inserted across the fracture into the head of the femur are widely used to immobilize the break to permit healing. The trailing end of the screw is usually supported by the tubular extension of a cortical side plate through which the nail can slide when some shortening of the neck takes place during healing. Often, instead of a side plate, an intramedullary rod with a transverse opening through which the nail can slide is used.

Because the fracture will be more stabilized if the broken ends are compressed together, particularly high neck fractures, screw devices that pull the base of the screw through the tubular support towards the side plate have been devised. While this also helps prevent harmful rotation of the bone ends on each other, a large number of devices have been devised to further prevent this rotation, such as keys and keyways in the tubular support. One of the problems with this approach is that it is difficult to correlate the rotation of the screw or nail with the optimal rotational position of the barrel and its side plate, especially if a device such as a nail with tangs has already been deployed.

While some devices have met some of these requirements, many have not. It is the aim of this invention to provide an easy to use and easy to manufacture apparatus that supports the trailing end of a fixing device, either a lag screw or a nail with locking tangs and enables initial compression of the bone ends together and continued compression while the fixing device is enabled to slide laterally, while at the same time, prevented from rotating.

SUMMARY OF THE INVENTION

The apparatus consists of a cortical side plate that is affixed to the proximal end of the femur with screws, with the proximal end of the side plate comprising a tubular barrel configured to extend into an opening in the lateral cortex of the femur and to support the trailing end of a lag screw or other fixing device. The section of the barrel supporting the screw, at least half of the barrel, is cylindrical, while the outer section of the barrel is polygonal in cross-section. After the barrel and trailing end of the screw have been positioned within the bone, an elongate cylindrical sleeve on which a sliding collar with a polygonal periphery has been fitted, is then positioned in the polygonal bore of the barrel, with the tabs on its leading end mating with notches on the trailing end of the screw, creating a non-rotatable junction. The sleeve has a series of kerf cuts along its length permitting it to expand and contract and its bore has a conical taper with the base of the cone towards its trailing end.

An elongate cylindrical plug having a matching conical taper and with external screw threads at its leading end is positioned within the bore of the sleeve, and screwed into the mating internal threads of the base of the lag screw or nail, just short of an expanding contact with the inner surface of the sleeve, so that while the base of the nail and sleeve are drawn together, the sleeve is not yet expanded, allowing the collar to slide freely. The trailing end of the elongate plug has an elongate central threaded opening for use with a tool, (not shown), and also a screw-driver slot.

A tool (not shown) is positioned at the trailing end of the device and is then used to push the polygonal collar forward on the sleeve, while at the same time exerting a traction force on the base of the elongate plug by means of its central threaded opening, thereby compressing the broken bone ends together. While compression is being maintained, the elongate plug is then advanced further into the sleeve causing the sleeve to expand, thereby locking the collar on the sleeve and maintaining the compression of the fracture but still permitting the sleeve to slide within the polygonal bore of the barrel.

The result is that the broken bone ends are compressed together by means of the lag screw threads or the tangs of a nail and the support apparatus, while at the same time the fixing device is prevented from rotating, but is nevertheless allowed to slide freely laterally, while maintaining the compression.

ADVANTAGES

An easy to use assembly that combines three essential functions, compression of the fracture, prevention of rotation and free sliding, in one device.

Apart from the screw or nail and the side plate and barrel, it has only three moveable parts.

Readily adaptable for use with fixing devices such as lag screws or nails with tangs.

Avoids the problem of correlating the axial rotation of fixing devices with the rotation of cortical side plates, since even a slight misapplication of a side plate can lead to hardware failure.

Decreased bulk over the end of the device with a corresponding decrease of subcutaneous irritation.

DETAILED DESCRIPTION OF THE DRAWINGS

Figure 1:
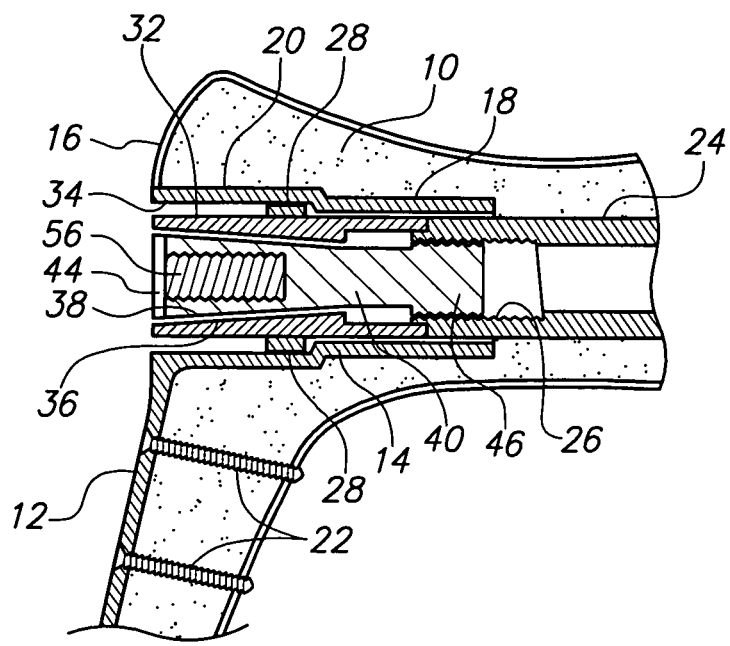
FIG. 1 is a sectional view of the apparatus deployed within a proximal femur.

FIG. 1 shows in detail the device deployed within a bone, in this example, a proximal femur 10. It is attached to the cortex 16 of the bone by means of screws 22. The proximal end of the side plate 12 comprises a tubular barrel 14. The barrel comprises two sections, the first end of the barrel comprising a cylindrical bore 18, and the second end of the barrel's bore comprising a polygonal section 20. In one embodiment, the polygonal section comprises an eight sided or octagonal configuration. The greater number of sides confers the ability of the barrel to have a thinner sidewall, and thus an overall decrease in bulk, at the cost of requiring greater machining tolerance to prevent slippage of a polygonal collar 28 within the polygonal bore 34 of the barrel.

A part of the base of a lag screw or nail 24 is shown in a sliding relationship with the end section 18 of the barrel.

An elongate tubular sleeve 32 is shown in sliding apposition within the barrel 18. The sleeve shown in FIGS. 1 and 3 comprises tabs 48 at its leading end, in one embodiment, two in number, that interact with notches 50 at the trailing end of the lag screw 24 to form a non-rotating junction. The diameter of the body of the sleeve 32 is similar to that of the lag screw 24.

The sleeve 32 has longitudinal kerf cuts 52, which are notched 54 at the trailing end of the sleeve to enable their use with a tool with tabs (not shown).

The bore of the sleeve 32 is conically tapered, 36, with the larger diameter at the trailing end of the bore.

An elongate generally cylindrical tapered plug 40 with a taper 38 matching the taper 36 of the sleeve 32 is positioned within the bore of sleeve 32. The leading end of the plug comprises external threads 46 matching the internal threads 26 of the lag screw or nail 24.

The length of the plug and the length of the sleeve relative to each other is predetermined so that when the leading end of the sleeve and the trailing end of the lag screw or nail are in apposition, and the threads 46 at the leading end of the plug and the internal threads 26 of the base of the screw or nail have become functionally engaged, the external taper 38 of the plug and the internal taper 36 of the sleeve are in close apposition to each other and require only an additional rotation or less, of the tapered plug into the tapered sleeve to become fully engaged and cause expansion of the sleeve, with a resulting locking of the collar 28 on the sleeve.

The sleeve 32 has a collar 28. The collar is polygonal, 30, and in one embodiment, octagonal, with a circular opening 42, that provides a sliding fit over the sleeve. When the sleeve is expanded by the tapered plug 40, the collar 28 is locked in place by a high static friction.

Since the sleeve is locked to the base of the lag screw or nail, and the collar is locked to the sleeve and unable to rotate but can slide in the octagonal barrel, the screw or nail together with the compressed fracture, is unable to rotate, but is able to slide freely.

When deploying the support assembly, prior to the locking of the collar 28 on the sleeve 32, a tool (not shown) is used to apply longitudinal pressure on the collar 28 causing it to slide on the sleeve 32 further into the polygonal section of the barrel 20 towards the cylindrical section of the barrel 18, while simultaneously applying traction to the base of the plug 40 by means of a draw bar (not shown) threaded into the threaded opening at the base of the plug, thereby causing the broken ends of the bone to become drawn together. The tapered elongate plug 40 is then advanced slightly further into the sleeve causing it to expand, locking the components of the assembly in place.

Figure 2:
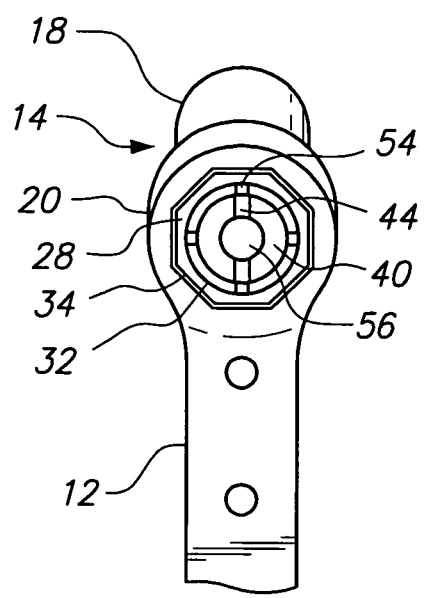
FIG. 2 is a side view of the device within the barrel of a cortical side plate.

FIG. 2 is a side view of the device in the polygonal section 20 of the tubular barrel 14, with the cylindrical section 18 of the barrel. The polygonal collar 28 is shown in the polygonal bore 34. The proximal end of sleeve the 32 shows the widened kerf cuts 54 for use with a tool (not shown). Also shown is the proximal end of the tapered plug 40 with its screw-driver slot 44 and the central threaded opening 56.

Figure 3:
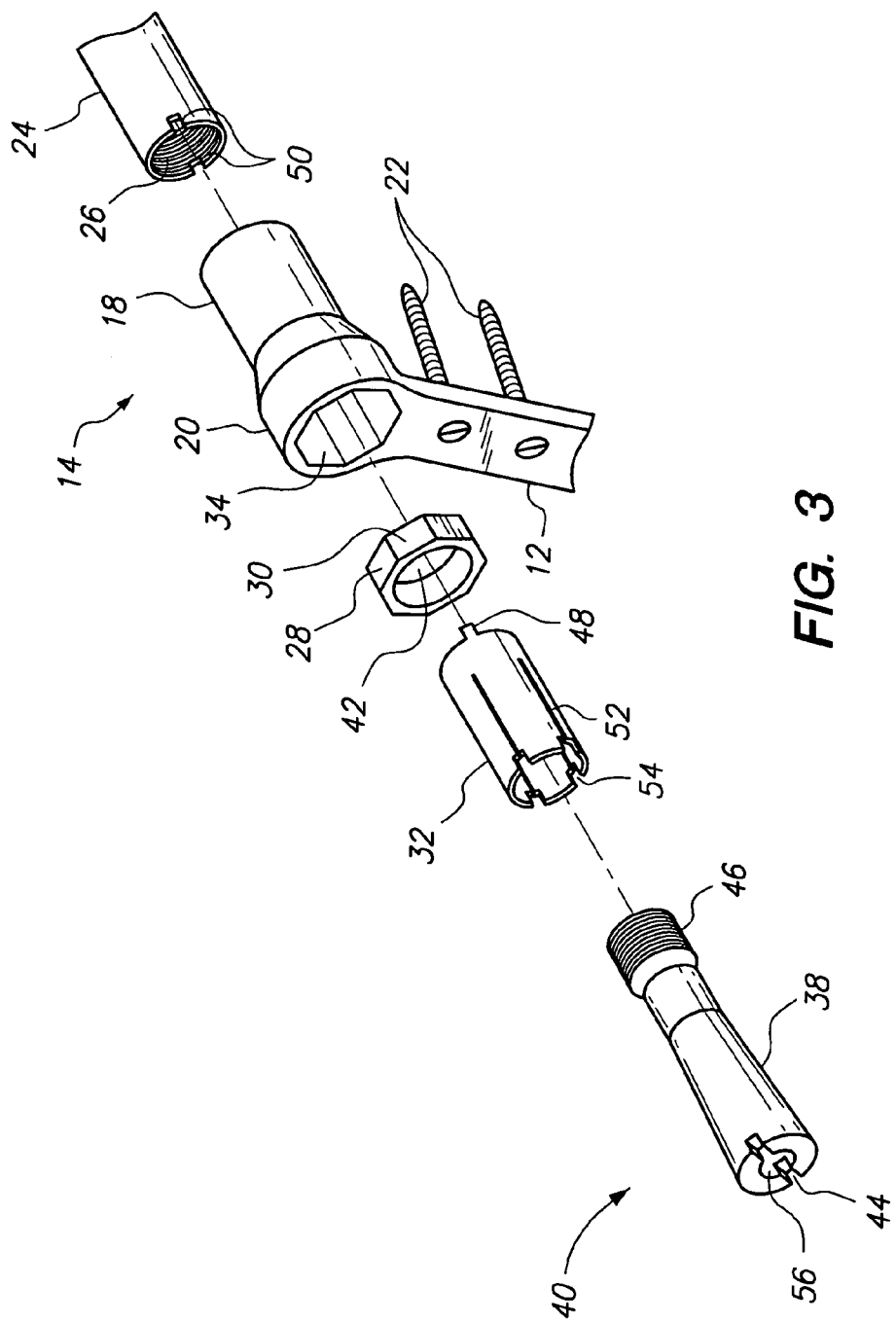
FIG. 3 is an exploded view of the device with the trailing end of a lag screw or nail.

FIG. 3 is an exploded view of the device showing the method of assembly of the components within the tubular barrel 14 with its cortical side plate 12, and fastening screws 22. The tapered plug 40 with its taper 38 and threaded end 46 is fitted into the internally tapered sleeve 32. The sleeve has longitudinal kerf cuts 52, each with notches 54 at their open end, and with tabs 48 that interdigitate with the notches 50 in the base of the screw or nail. The collar 28 slides over the sleeve 32 and the plug 40, to form a unit that slides into the polygonal bore 34, to engage with the base of the screw 24, its notches 50, and its internal threads 26.

| Reference Numerals. | |
|---|---|
| 10 | Femoral bone |
| 12 | Cortical Side Plate |
| 14 | Tubular Barrel |
| 16 | Cortex of Bone |
| 18 | Cylindrical Section of Barrel |
| 20 | Polygonal Section of Barrel |
| 22 | Screws |
| 24 | Lag Screw or Nail |
| 26 | Lag screw or Nail Internal Threads |
| 28 | Collar |
| 30 | Polygonal Circumference |
| 32 | Sleeve |
| 34 | Polygonal Bore |
| 36 | Taper of sleeve |
| 38 | Taper of Plug |
| 40 | Tapered Plug |
| 42 | Circular opening |
| 44 | Screw driver Slot |
| 46 | External Plug Threads |
| 48 | Sleeve Tabs |
| 50 | Notches |
| 52 | Kerf Cuts |
| 54 | Kerf Cut Notches |
| 56 | Threaded opening |

I claim:

1. A hip nail support assembly comprising:

a fastener comprising a lag screw or hip nail, said fastener comprising a leading end and a trailing end, the trailing end comprising internal threads;

a cortical side plate, said plate comprising a first end and a second end, the first end of the plate comprising an angularly disposed tubular barrel with a first end, a second end, a bore throughout the barrel, and a longitudinal axis, said barrel configured to extend into an opening in a cortex of a bone, wherein the bore of at least half of the first end of the barrel is cylindrical in shape and configured for a sliding relationship with the trailing end of the fastener, the bore at the second end of the barrel being polygonal in shape along the longitudinal axis of the barrel;

a ring-like collar, said collar comprising a polygonal circumference, said circumference enabling a sliding non-rotating relationship of the collar with the bore at the second end of said barrel, and a central circular opening, said opening having a diameter which is substantially similar to that of the trailing end of the fastener;

an elongate cylindrical tubular sleeve configured to be positioned longitudinally within the opening of the collar, the sleeve comprising a first end, a second end, a central bore, a plurality of kerf cuts along its length, and an external diameter, wherein the external diameter of the sleeve is substantially similar to the diameter of the opening in said collar, whereby said collar encircles said sleeve and enables a sliding relationship with said sleeve, the first end of the sleeve comprising a plurality of tabs, each of the plurality of tabs configured to interdigitate with each of a plurality of similarly configured notches in the trailing end of the fastener to enable a non-rotatable engagement between the sleeve and fastener, the central bore of said sleeve comprising a conical taper, with a base of the conical taper towards the second end of the sleeve, the plurality of kerf cuts enabling said sleeve to expand or contract, and each of the plurality of kerf cuts comprising a notch at the second end of the sleeve to enable engagement with a tool; and an elongate conical tapered plug positioned longitudinally within the central bore of said sleeve, said plug comprising a first end, a second end, a taper, and a longitudinal axis, said taper of the plug matching the conical taper of the central bore of the sleeve, said first end of the plug comprising external threads enabling engagement with the internal threads of the trailing end of the fastener, the second end of the plug comprising a longitudinally directed threaded opening for engagement with a threaded tool and a means for rotating the plug about the longitudinal axis of the plug, said means comprising a screwdriver slot;

wherein, when the sleeve is positioned within the opening of the collar and the plug is positioned within the central bore of the sleeve such that the taper of the plug is in close apposition with the conical taper of the central bore of the sleeve, the plug is translated in the direction of the first end of the plug, thereby causing expansion of said sleeve and a high static friction between the sleeve and the surrounding collar, resulting in a locking engagement between the sleeve and collar, said plug being greater in length than said sleeve thereby enabling the external threads of the first end of said plug to engage with the internal threads of the trailing end of the fastener when the taper of the plug is in close apposition with the conical taper of the central bore of the sleeve but prior to expansion of the sleeve.

2. The apparatus of claim 1, wherein said bore at the second end of said barrel is octagonal, and said polygonal circumference of said collar is octagonal.

3. The apparatus of claim 1, wherein said plurality of kerf cuts of said sleeve comprises four kerf cuts.

4. The apparatus of claim 3, wherein the plurality of tabs of the first end of said sleeve comprises two tabs, and the plurality of notches in the trailing end of the fastener comprises two notches.

* * * * *